United States Patent
Montagnon et al.

(10) Patent No.: US 6,267,921 B1
(45) Date of Patent: Jul. 31, 2001

(54) NICKEL-FREE STAINLESS STEEL FOR BIOMEDICAL APPLICATIONS

(75) Inventors: Jacques Montagnon, Clermont-Ferrand; Jean-Yves Moraux, Paris, both of (FR)

(73) Assignee: Societe Industrielle de Metallurgie (FR)

( * ) Notice: Subject to any disclaimer, the term of this patent is extended or adjusted under 35 U.S.C. 154(b) by 0 days.

(21) Appl. No.: 09/445,171

(22) PCT Filed: Jun. 4, 1998

(86) PCT No.: PCT/FR98/01130

§ 371 Date: Dec. 3, 1999

§ 102(e) Date: Dec. 3, 1999

(87) PCT Pub. No.: WO98/55662

PCT Pub. Date: Dec. 10, 1998

(30) Foreign Application Priority Data

Jun. 4, 1997 (FR) .................................................. 97 06863

(51) Int. Cl.[7] .......................... C22C 38/24; C22C 38/22; C22C 38/38
(52) U.S. Cl. ................. 420/57; 420/59; 420/79; 148/327; 623/924
(58) Field of Search ................. 420/57, 59, 79; 148/327; 623/924

(56) References Cited

U.S. PATENT DOCUMENTS

| | | | |
|---|---|---|---|
| 3,904,401 | * 9/1975 | Mertz et al. ............... | 420/57 |
| 4,523,951 | * 6/1985 | Andreini et al. ............ | 420/57 |
| 5,094,812 | * 3/1992 | Dulmaine et al. ........... | 420/57 |

FOREIGN PATENT DOCUMENTS

| | | |
|---|---|---|
| 684979 | 2/1995 | (CH) . |
| 9215141 | 1/1993 | (DE) . |
| 0422360 | 4/1991 | (EP) . |
| 2071667 | 9/1971 | (FR) . |
| 506905 | 6/1939 | (GB) . |
| 9116469 | 10/1991 | (WO) . |

* cited by examiner

*Primary Examiner*—Deborah Yee
(74) *Attorney, Agent, or Firm*—Ostrolenk, Faber, Gerb & Soffen, LLP

(57) ABSTRACT

The invention concerns a high specification non-magnetic stainless steel which is corrosion resistant in physiological media and which can be produced at atmospheric pressure, characterized in that its composition in % by weight is as follows:

| | | | |
|---|---|---|---|
| Mn | 15% to 24% | Ti | ≦0.020% |
| Cr | 15% to 20% | Al | ≦0.020% |
| Mo | 2.5% to 4% | S | ≦0.0020% |
| N | 0.6% to 0.85% | B | ≦0.020% |
| V | 0.1% to 0.5% | Nb + Ta | ≦0.5% |
| C | ≦0.06% | Co | ≦0.5% |
| Ni | ≦0.25% | Cu | ≦0.5% |
| silica | ≦0.25% | | | and from 0 to 0.5% of each of elements Cu, Co and of the sum Nb+Ta, the remainder being constituted by iron and impurities, and in that its composition satisfies the following conditions:

$$(\%Cr)+2.5(\%Mo) \leq 27 \quad \text{(I)}$$

$$(\%Cr)+3.3(\%Mo) \geq 26 \quad \text{(II);}$$

and $$\text{Log}(\%N)+0.0605(\%N)=-1.3+[125(\%V)+80(\%Nb)+52(\%Cr)+19(\%Mn)]\times 10^{-3}-[4.3(\%Cr)^2+0.35(\%Mn)^2]\times 10^{-4}+0.17(\%Cr)^3\times 10^{-5} \quad \text{(III).}$$

19 Claims, No Drawings

NICKEL-FREE STAINLESS STEEL FOR BIOMEDICAL APPLICATIONS

This application is a 371 of PCT/FR98/01130 filed Jun. 4, 1998.

The invention relates to a grade of nickel-free austenitic stainless steels which is corrosion resistant in physiological media, and which can satisfy all of the minimum values for characteristics and properties specified in the International Organization for Standardization (ISO) standard 5832-1 "Wrought stainless steels for surgical implants" and which can be produced in conventional furnaces without any special apparatus for pressurizing the furnace.

The very low residual nickel content in that class of steel can cause allergic reactions to that element on internal and/or external application in or on the human body.

WO91/16469 discloses a non-magnetic austenitic stainless steel having, in particular, both mechanical properties and good corrosion resistant properties under stress. That steel has a composition that is designed to be used in drilling equipment and which consequently is not affected by the problems of nickel leaching into physiological media.

Unfortunately, in the biomaterials field, the trend in legislation in a number of countries is currently towards limiting or even eliminating nickel from alloys which come into contact with skin or which are used to manufacture temporary (bone reconstruction) or permanent (prosthesis) prosthetic material. It has been known for a number of years that nickel ions leach from certain biomaterials into the human body and can lead to localized irritation and even to infection in some cases. Intracutaneous tests have shown that 15% of the population can be susceptible to allergic reactions to nickel.

Austenitic stainless steels alloyed with nickel are particularly important in this regard because they are widely used to produce parts which are implanted or parts which come merely into contact with the human body, such as:
temporary or permanent bone implants;
external fracture reduction fixings;
watches and watch straps.

Such steels alloyed with nickel have until now been used because of their excellent compromise between their various characteristics, such as intrinsic mechanical strength, stability against a variety of different forms of corrosion, and surface resistance, for example frictional resistance.

The implant field, currently the most critical as regards risks of allergy, has formed the basis for studying the steel of the present invention.

In this field, the use of alloys other than such steels has suffered from technical shortcomings or economic problems connected with the cost of such materials or their implementation.

According to the recommendations of the ISO system, austenitic steels can currently be used to produce implants for human use; such steels are defined in ISO standards 5832/1 and 5832/9. Their nickel content must be in the range 9% to 15% and their use can thus result in nickel leaching even in the absence of any corrosion mechanism developing.

The passive film which coats them and endows them with corrosion stability can leach nickel ions as a result of mechanical defects under frictional conditions or as a result of electrochemical equilibria with the surrounding medium, which involves slow simultaneous dissolution and reconstruction of that surface film.

Further, nickel-containing austenitic stainless steels are known to be sensitive to stress corrosion mechanisms or to fatigue corrosion mechanisms when they are subjected to stresses which exceed a certain "threshold" in relation to plastification of micro-domains in contact with the corrosive medium: nickel contributes to the development of these corrosion mechanisms, which are particularly disastrous since they can result in the part breaking.

Nickel-free ferritic steels which are more resistant to stress corrosion cannot be used as human implants because of their ferromagnetic properties.

According to ISO standard 5832-1, in order to provide corrosion stability in physiological media, chromium, which endows steels with stainless properties beyond a minimum content of about 13% and molybdenum which completes and substantially stabilizes the stainless nature of chromium steels, must both be added in amounts which are capable of satisfying the following relationship:

$$(\%Cr)+3.3(\%Mo) \geq 26,$$

expressed as the concentration by weight of the alloying elements.

In addition to chromium and molybdenum, manganese-containing austenitic stainless steels contain different proportions of manganese and nitrogen which modify their stainless nature: manganese, which is less noble than nickel in the electrochemical series, substantially affects the corrosion stability of stainless steels, while nitrogen is known to improve it.

Recent studies have tended to show that to a first approximation, the corrosion stability of manganese stainless steels in chlorinated media is linked to their composition as regards the principal alloying elements in accordance with the following relationship:

$$(\%Cr)+3.3(\%Mo)+30(\%N)-(\%Mn)$$

which give a value that characterizes the corrosion stability of such steels.

Thus the higher the value, the better the corrosion stability of the steel.

Preferably, the proportion of alloying elements is such that:

$$(\%Cr)+3.3(\%Mo)+30(\%N)-(\%Mn) \geq 26$$

so as to obtain corrosion stability in the media of the envisaged application which is at least equivalent to that of grade D as described in ISO standard 5832-1.

Austenitic stainless steels containing manganese can contain carbon, with the aim of stabilizing the austenitic structure. However, adding carbon even in amounts as low as 0.1% by weight leads to a very substantial degradation in corrosion stability. Carbon forms carbides with the elements chromium and molybdenum in particular, and as a result the austenitic matrix located around the carbides is depleted in the elements chromium and molybdenum which are nevertheless present to endow the steel with stainless properties. Types of corrosion rather like intergranular corrosion can develop. Further, carbon degrades stress corrosion stability.

In the precise case of applications in physiological media, the carbon content of a stainless steel must remain below 0.1% by weight, preferably below 0.06%.

Because of the above technical problems connected with known steels, there currently exists strong demand, which the invention intends to satisfy, for non-magnetic austenitic stainless steels with a very low nickel content and with the following properties:
no ferromagnetism;
a mechanical strength equal to or greater than that of existing steels described in ISO standards 5832/1 and 5832/9, with no brittleness;

a corrosion stability in physiological media which is substantially better than or equal to that of the steel defined by ISO standard 5832/1;
able to take a high polish;
good fatigue behavior;
better resistance to stress corrosion in physiological media up to stresses approaching their 0.2% conventional elastic limit;
very low numbers of inclusions and undesirable residual elements;
manufacturing costs equivalent to or lower than those of traditional austenitic steels, in particular as regards developing a specific alloy composition which can be produced by conventional means without a remelting step carried out under high nitrogen pressure; and
good hardening capabilities by work hardening.

The invention achieves these aims by providing a steel with the following composition as percentages by weight:

15% to 20% of Cr;
2.5% to 4% of Mo;
15% to 24% of Mn;
0.6% to 0.85% of N;
0.1% to 0.5% of V;
0 to 0.25% of Ni;
0 to 0.06% of C;
0 to 0.25% of Si;
0 to 0.02% of B;
0 to 0.5% of Nb+Ta;
0 to 0.5% of Co;
0 to 0.5% of Cu;
0 to 0.002% of S;
0 to 0.02% of Ti;
0 to 0.02% of Al;

the remainder is constituted by iron and impurities, and the conditions are as follows:

$$(\%Cr)+2.5\,(\%\,Mo)\leq 27 \quad (I)$$

$$(\%Cr)+3.3(\%Mo)\geq 26 \quad (II);$$

and $$Log(\%N)+0.0605(\%N)=-1.3+[125(\%V)+80(\%Nb)+52(\%Cr)+19(\%Mn)]\times 10^{-3}-[4.3(\%Cr)^2+0.35(\%Mn)^2]\times 10^{-4}+0.17(\%Cr)^3\times 10^{-5} \quad (III)$$

In a preferred composition, $$(\%Cr)+3.3(\%Mo)+30(\%N)-(\%Mn) \text{ is 26 or more} \quad (IV).$$

Advantageously, the $R_p$ 0.2 tensile yield strength is 450 N/mm$^2$ or more after solution treatment at a temperature or 1000° C. or more and overhardening.

More particularly, the tensile yield strength, $R_p$ 0.2, is 1000 N/mm$^2$ or more and the elongation at rupture, A5d, is more than 25% after ambient temperature work hardening of the metal solution treated at a temperature of 1000° C. or more and overhardening.

The invention also relates to the use of the above steel to produce parts intended to come into contact with the human body, in particular tissue, for internal or external application.

The steel of the present invention is constituted by a purely austenitic structure after solution treatment at above 1000° C., even though its composition does not include the addition of the elements carbon and nickel that are normally used in different proportions to stabilize the austenite of chromium- and molybdenum-rich steels. The maximum values of the nickel and carbon contents of the steel of the present invention are thus respectively 0.06% and 0.25%, with the precise aim of producing a steel which is resistant to intergranular corrosion and to stress corrosion, and of eliminating the leaching of nickel ions from the passive film coating it, when the steel is used as a biomaterial in contact with human tissue.

One particular feature of the steel of the invention is that its austenitic structure is exclusively stabilized by the gammagenic elements nitrogen, manganese and optionally boron, in the absence of nickel and carbon, which are then considered to be residual impurities. Gammagenic elements encourage and/or stabilize the face centered cubic crystallographic phase of gamma austenite. Impurities are inevitable with the production means used such as an arc furnace, an AOD reactor (argon, oxygen, decarburization converter) or standard slag remelting processes without a particular means in the production furnace for placing it under nitrogen pressure.

The elements cobalt and copper, which are also austenite stabilizers and which are found as impurities in different quantities in the starting materials required for producing stainless steels, are strictly limited to a maximum content of 0.5% each, for the following reasons:

cobalt is a metallic element which has been cited as a metal which can be toxic to the human body;

copper is an element having a number of advantages when added to stainless steels, such as improving machinability and corrosion stability. However, the prior art has not envisaged that adding copper can irretrievably degrade the forgeability of stainless steels with a high manganese content such as those of the present invention when they are cast into ingots, as a result of formation in the ingots of a very low melting point compound based on manganese and copper, which is caused by segregation.

Finally, copper and cobalt severely limit the solubility of nitrogen in liquid steel during production by conventional means without production furnace pressurization apparatus; nitrogen is indispensable for producing the required properties.

For the reasons given above, the copper and cobalt contents of the steel of the invention are strictly controlled to less than 0.5% each.

A further important feature of the steel of the invention is that the chromium and molybdenum contents must be such that (Cr%)+2.5(Mo%)≦27. Using conventional production means, with no furnace pressurization apparatus and imposing a partial saturating pressure of nitrogen in the liquid metal, the steel of the present invention is purely austenitic when its composition satisfies at least the above condition.

The specific roles of each of the major additive elements of the steel of the invention can be detailed as follows:

Chromium is the major element for constructing the passive film which protects the metal from corrosion. Despite its intrinsic alphagenic tendency, it also plays a major role in producing austenitic steel since it greatly encourages nitrogen solubility, in particular in liquid steel. Alphagenic elements encourage and/or stabilize the body centered cubic crystallographic phase of alpha ferrite which is stable at low temperatures, and of the delta ferrite which is stable at high temperatures. Given the sigmagenic role of chromium, its content is preferably limited to 20%. Sigmagenic elements are those which encourage and/or stabilize the sigma phase which is a very hard block intermetallic compound of the Fe—Cr—Mo system.

Molybdenum participates strongly in localized corrosion resistance in reducing chloride media; thus its addition in the highest possible quantities is indispensable in biomedical applications. However, this element is both highly alphagenic and sigmagenic and also raises the solution temperature of the sigma phase. In contrast to chromium, it does not greatly encourage nitrogen solubility and finally it has a marked tendency to segregate in the ingot. For these reasons, the maximum molybdenum content is limited to 4%.

Manganese is an element which directly stabilizes austenite. Further, it increases the solubility of nitrogen in the liquid steel, but to a lesser extent than chromium. Finally, associated with nitrogen, it substantially encourages hardening of the austenite during cold work hardening. However, its maximum content is fixed at 24% because of its tendency to embrittle the steel at forging temperatures by forming intermetallic phases, and for its deleterious influence at high concentrations on the corrosion stability of stainless steels.

Nitrogen is the principal stabilizing element of austenite; to this end, its content must be at least 0.6%. This element can also increase corrosion stability and the mechanical strength of the steel. Excessive addition of nitrogen must be avoided to prevent blowholes from forming when the ingots solidify, and the precipitation of nitrides at solution temperatures.

Further, the nitrogen content is limited to a maximum value of 0.85% as higher contents cause the austenite to become brittle, in particular when work hardening is carried out, the ductile/brittle transition temperature increases in proportion to the nitrogen content and gets close to the service temperature range.

The maximum nitrogen content is naturally given by its solubility in the liquid steel, at given temperatures and pressures. The steel of the invention has nitrogen added in proportions enabling it to be produced at atmospheric pressure with conventional means (arc furnace, AOD, remelting furnace under slag) and also effectively stabilizing the austenite.

These specific properties are obtained when the nitrogen content (N) in the steel of the invention satisfies the relationship:

$$\text{Log}(\%N)+0.0605(\%N)=-1.3+[125(\%V)+80(\%Nb)+52(\%Cr)+19(\%Mn)]\times10^{-3}-[4.3(\%Cr)^2+0.35(\%Mn)^2]\times10^{-4}+0.17(\%Cr)^3\times10^{-5}$$

Added vanadium is a particular feature of the steel of the invention. This element increases the solubility of nitrogen in liquid steel during production, which enables the nitrogen content of the steel to be adjusted to higher values, within the indicated limits. However, increasing vanadium content extends the vanadium nitride stability region and in particular raises its solvus temperature. To retain a purely austenitic steel after the recommended solution treatment and overhardening, the maximum vanadium content is limited to 0.5%.

Boron stabilizes austenite strongly. In contrast, its limited solubility in the steel of the invention does not enable a large amount to be added. Its content is thus limited to 200 ppm.

Since they are capable of modifying phase equilibria, and also because they produce hard compounds which do not produce a perfect surface state when the steel is polished, the carburigenic elements niobium and tantalum must be limited to a strict minimum required for the characteristics supplied by these elements, such as stabilization of the carbon in the steel.

Of the elements which constitute residual impurities in the steel, some must be strictly controlled and limited to very low values since they degrade the desired properties.

Sulfur content is limited to 20 ppm with the precise aim of avoiding intergranular brittleness which this element causes at any temperature, in particular at forging temperatures, but also to reduce to as small a value as possible the amount of non-metallic inclusions which this element forms, in particular with manganese.

Silicon, which is favored for certain aspects such as deoxidation of liquid metal, is limited to a level of 0.25% or less, since this element is a powerful sigma phase producer which is deleterious to corrosion stability in general. It is also an element which encourages segregation in ingots—a phenomenon which is not to be encouraged.

The elements titanium and aluminum must be strictly controlled so as to avoid or limit the formation of their nitrides which have very low solubilities, and which uselessly fix a fraction of the nitrogen in the form of hard and embrittling compounds. They are limited to a maximum content of 0.02%.

After heat solution treatment and overhardening from a temperature of more than 1000° C., and for dimensions equal to at least those of the products manufactured for the envisaged applications, the steel of the invention has the properties required.

Its structure is purely austenitic and non ferromagnetic.

After treatment, with the features defined above, its minimum characteristics are as follows:

Maximum tensile strength: $Rm \geq 800$ N/mm$^2$
Tensile yield strength: $Rp0.2 \geq 450$ N/mm$^2$
Elongation at rupture (the base measurement being 5 times the diameter of the sample): $A5d \geq 40\%$ In addition, its toughness is excellent.

After cold working, the Rp0.2 tensile yield strength of bars can reach 1100 N/mm$^2$, while the elongation at break remains above 25%, which exceeds the characteristics of the steels defined in ISO standard 5832-1.

For a work hardened steel yield strength of 1300 N/mm$^2$, the elongation at rupture remains 10% or more.

Its corrosion resistance can be evaluated using an electrochemical test specific to the extreme conditions encountered in the case of localized crevice corrosion in chloride media; the test medium is constituted by an aqueous solution containing 2 moles of sodium chloride and is acidified to a pH of 1.2 by adding hydrochloric acid.

The table below shows the results of this test on two cast steels of the invention A and B, compared with a cast steel C satisfying the criterion (%Cr)+3.3(%Mo)$\geq$26 which mirrors the composition of the invention with the exception of the fact that (%Cr)+3.3(%Mo)+30(%N)−(%Mn) is less than 26, and compared firstly with a prior art austenitic manganese-containing cast steel D which does not satisfy the above two conditions, and a cast steel E as described in ISO standard 5832-1 and where the corrosion resistance acts as a reference.

The dissolution current densities measured at the maximum of the activity peak provides an idea of the rate at which metal is corroded in the medium under consideration, i.e., the higher the current density, the faster the metal corrodes. The value of the rupture potential translates as the stability of the metal passivation; the higher the potential, the more the metal will resist triggering a localized corrosion mechanism. The results of these tests, shown in the table below, show:

a) the best resistance to triggering localized corrosion mechanisms was shown by cast steels A and B of the invention. Both had a rupture potential higher than that of steel E of ISO standard 5832-1, and the values remained high even under the high acidification conditions of the medium;

b) cast B of the invention and cast E (ISO 5832-1) had substantially equivalent active corrosion stabilities in a reducing acid medium;

c) cast A of the invention had a slightly higher activity compared with cast B: this effect can be attributed to the low molybdenum content of cast A, which content is very close to the minimum value specified for the steel of the invention;

d) good agreement of the relationship (%Cr)+3.3(%Mo)+30(%N)−(%Mn) with the corrosion stability of stainless steels alloyed with manganese; classification of the corrosion stability of steels in chloride solutions such as a physiological medium is more precise with the above relationship than when using the conventional relationship (%Cr)+3.3(%Mo) as the first emphasizes the very beneficial role of nitrogen and the pernicious influence of manganese;

e) the corrosion stabilities of casts C and D, which did not satisfy all of the characteristic prescriptions of the composition of the invention, are worse than that of cast E; in the case of cast D, this result is justified by its very low molybdenum content while in the case of cast C, the high molybdenum content is not sufficient to compensate for the loss of corrosion stability induced by small chromium and nitrogen contents and high manganese contents.

Admittedly, the recorded metal/solution exchange currents in the absence of corrosion are of the order of ten $\mu A \cdot cm^{-2}$ for stainless steels. This means that the three casts A, B and E in the medium with a high chloride concentration, acidified to a pH of 1.2, are practically in a passive state and that this passive state can be ensured by a slightly higher pH.

However, such acidity cannot be encountered in the natural state in the human body. The surrounding medium is gradually acidified by its reaction with the corrosion products only after localized corrosion (crevice type) develops.

Admittedly again, the essential beneficial role of the nitrogen in the stainless steels as regards their localized corrosion behavior is solely to significantly neutralize this effect by a chemical reaction.

The nitrogen liberated by the corrosion phenomenon causes alkali ions to form which neutralize the local acidification.

It can be deduced that, in addition to the good resistance shown by the initiation of localized forms of corrosion, the steels of the invention behave particularly well as regards stability against other forms of corrosion.

| Composition wt % | Cast A | Cast B | Cast C | Cast D | Cast E (ISO 5832-1) |
|---|---|---|---|---|---|
| C | 0.037 | 0.052 | 0.045 | 0.035 | 0.012 |
| Si | 0.179 | 0.18 | 0.215 | 0.041 | 0.31 |
| Mn | 21.17 | 21.1 | 23.65 | 18.70 | 1.80 |
| Ni | 0.22 | 0.21 | 0.25 | 0.24 | 14.64 |
| Cr | 17.83 | 17.56 | 14.85 | 18.52 | 17.29 |
| Mo | 2.69 | 3 | 4.03 | 0.390 | 2.74 |
| N | 0.70 | 0.694 | 0.623 | 0.61 | 0.08 |
| V | 0.11 | 0.1 | 0.1 | 0.05 | — |
| B | — | — | — | — | — |
| Nb + Ta | 0.020 | <0.020 | <0.010 | <0.010 | — |
| Co | 0.33 | 0.031 | <0.010 | 0.01 | 0.06 |
| Cu | 0.36 | 0.34 | 0.017 | 0.028 | 0.05 |
| S | 0.0013 | 0.0014 | 0.0019 | 0.0004 | <0.002 |
| Ti | <0.010 | <0.010 | <0.010 | <0.010 | — |
| Al | 0.016 | 0.009 | 0.018 | 0.0031 | — |
| Cr + 2.5 Mo | 24.55 | 25.05 | 24.92 | 19.5 | 24.14 |
| Cr + 3.3 Mo | 26.7 | 27.5 | 28.1 | 19.8 | 26.3 |
| Cr + 3.3 Mo + 30 N—Mn | 26.5 | 27.2 | 23.2 | 19.4 | 26.9 |
| i activity (1) ($\mu A \cdot cm^{-2}$) | 45 | 20 | 460 | 10000 | 15 |
| E rupture (2) | >500 mV/SCE | >500 mV/SCE | 100 to 350 mV/SCE | <−100 mV/SCE | <300 mV/SCE |

(1) Dissolution current density measured at the maximum activity peak during potentiokinetic electrochemical tests in an aqueous medium containing chloride (NaCl - 2M) and acidified to pH 1.2 by adding hydrochloric acid.
(2) Scanning anodic potentiokinetic potential in the above medium (1) from which the dissolution currents sharply increase connected with the initiation of corrosion points. The potential is measured with respect to a saturated calomel reference electrode (SCE).

What is claimed is:

1. A high specification non-magnetic stainless steel which is corrosion resistant in physiological media, and which can be produced at atmospheric pressure, characterized in that its composition in % by weight is as follows:

| | | | |
|---|---|---|---|
| Mn | 15% to 24% | Ti | ≦0.020% |
| Cr | 15% to 20% | Al | ≦0.020% |
| Mo | 2.5% to 4% | S | ≦0.0020% |
| N | 0.6% to 0.85% | B | ≦0.020% |
| V | 0.1% to 0.5% | Nb + Ta | ≦0.5% |
| C | ≦0.06% | Co | ≦0.5% |
| Ni | ≦0.25% | Cu | ≦0.5% |
| silica | ≦0.25% | | | and from 0 to 0.5% of each of elements Cu, Co and of the sum Nb+Ta, the remainder being constituted by iron and impurities, and in that its composition satisfies the following conditions:

$$(\%Cr)+2.5(\%Mo) \leq 27 \quad (I)$$

$$(\%Cr)+3.3(\%Mo) \geq 26 \quad (II);$$

and $$\mathrm{Log}(\%N)+0.0605(\%N)=-1.3+[125(\%V)+80(\%Nb)+52(\%Cr)+19(\%Mn)]\times 10^{-3}-[4.3(\%Cr)^2+0.35(\%Mn)^2]\times 10^{-4}+0.17(\%Cr)^3\times 10^{-5} \quad (III).$$

2. A steel according to claim 1, characterized in that said composition satisfies the relationship:

$$(\%Cr)+3.3(\%Mo)+30(\%N)-(\%Mn) \geq 26 \quad (IV).$$

3. A steel according to claim 1 characterized in that the $R_p$ 0.2 tensile yield strength is 450 N/mm² or more after solution treatment at a temperature of 1000° C. or more and overhardening.

4. A steel according to claim 1 characterized in that the $R_p$ 0.2 tensile yield strength is 1000 N/mm² and in that the A5d elongation at rupture is more than 25% after ambient temperature work hardening of the metal solution treated at a temperature of 1000° C. or more and overhardening.

5. A steel according to claim 2 characterized in that the $R_p$ 0.2 tensile yield strength is 450 N/mm² or more after solution treatment at a temperature of 1000° C. or more and overhardening.

6. A steel according to claim 2 characterized in that the $R_p$ 0.2 tensile yield strength is 1000N/mm² and in that the A5d elongation at rupture is more than 25% after ambient temperature work hardening of the metal solution treated at a temperature of 1000° C. or more and overhardening.

7. In a part having the surface which comes into contact with the human body, the improvement which comprises the surface being a steel according to claim 6.

8. In a part having the surface which comes into contact with the human body, the improvement which comprises the surface being a steel according to claim 5.

9. In a part having the surface which comes into contact with the human body, the improvement which comprises the surface being a steel according to claim 4.

10. In a part having the surface which comes into contact with the human body, the improvement which comprises the surface being a steel according to claim 3.

11. In a part having the surface which comes into contact with the human body, the improvement which comprises the surface being a steel according to claim 2.

12. In a part having the surface which comes into contact with the human body, the improvement which comprises the surface being a steel according to claim 1.

13. The part according to claim 12 in the form of an implant.

14. In a method of bringing the surface of a part into contact with the human body, the improvement which comprises utilizing a steel according to claim 6 as said surface.

15. In a method of bringing the surface of a part into contact with the human body, the improvement which comprises utilizing a steel according to claim 5 as said surface.

16. In a method of bringing the surface of a part into contact with the human body, the improvement which comprises utilizing a steel according to claim 4 as said surface.

17. In a method of bringing the surface of a part into contact with the human body, the improvement which comprises utilizing a steel according to claim 3 as said surface.

18. In a method of bringing the surface of a part into contact with the human body, the improvement which comprises utilizing a steel according to claim 2 as said surface.

19. In a method of bringing the surface of a part into contact with the human body, the improvement which comprises utilizing a steel according to claim 1 as said surface.

* * * * *